United States Patent [19]

Baiocchi

[11] Patent Number: 4,749,794

[45] Date of Patent: Jun. 7, 1988

[54] MANUFACTURING OF BENZYDAMINE PURIFICATION OF BENZYDAMINE USING STEAM DISTILLATION

[75] Inventor: Leandro Baiocchi, Rome, Italy

[73] Assignee: Aziende Chimiche Riunute Angelini Francesco A.C.R.A.F. S.p.A., Rome, Italy

[21] Appl. No.: 892,733

[22] Filed: Jul. 29, 1986

Related U.S. Application Data

[63] Continuation of Ser. No. 604,822, Apr. 27, 1984, abandoned, which is a continuation of Ser. No. 387,112, Jun. 10, 1982, abandoned.

[30] Foreign Application Priority Data

Jul. 1, 1981 [IT] Italy ................................ 22684 A/81

[51] Int. Cl.$^4$ ..................... C07B 63/00; C07D 231/20
[52] U.S. Cl. ......................................... 548/372; 203/95
[58] Field of Search ........................... 548/372; 203/95

[56] References Cited

U.S. PATENT DOCUMENTS 3,318,905   5/1967   Palazzo ........................... 548/372

FOREIGN PATENT DOCUMENTS 976173   10/1975   Canada ........................... 548/372
49-108070 10/1974   Japan ............................. 548/372

OTHER PUBLICATIONS

Vogel, "A textbook of Practical Organic Chemistry", 3rd Edition, Wiley, New York, 1962, pp. 12, 145.
Wiberg, K. B., "Laboratory Technique in Organic Chemistry", (1960), pp. 71-74.

*Primary Examiner*—John M. Ford
*Assistant Examiner*—Dale A. Bjorkman
*Attorney, Agent, or Firm*—Ladas & Parry

[57] ABSTRACT

A method for removing a 1-chloro-3-dimethylaminopropane impurity from a benzydamine crude product which comprises steam distillation.

6 Claims, No Drawings

MANUFACTURING OF BENZYDAMINE PURIFICATION OF BENZYDAMINE USING STEAM DISTILLATION

This is a continuation of co-pending application Ser. No. 604,822 filed on Apr. 27, 1984, now abondoned, which is a continuation of Ser. No. 387,112 filed June 10, 1982 now abandoned.

Benzydamine is the hydrochloride of 1-benzyl-3-dimethylaminopropoxy-1H-indazole (I) (C.A.S. Reg. No. 41533-84-0) and it is used as a systemic and topic antiflammatory agent in Western Europe and in several other Countries both in human and in animal therapy.

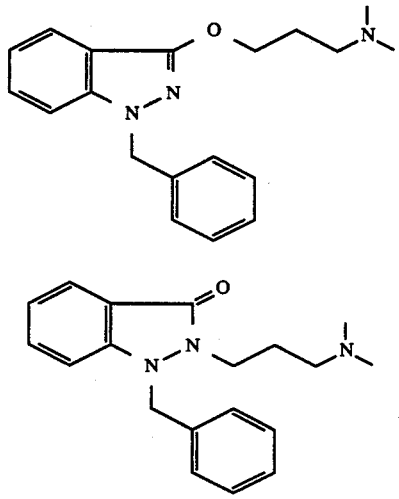

This compound is manufactured according to the method described for its 6-chloro analogue in the U.S. Pat. No. 3,318,905 (i.e. reacting an excess of the 1-chloro-3-dimethylaminopropane with 1-benzyl-3-hydroxy-1H-indazole sodium salt in refluxing xylene).

According to the cited U.S. Pat. No. 3,318,905 the reaction mixture is cooled, washed with water and the solvent is then removed.

The viscous residue thus obtained is distilled to give (I) base (b.p. 160° C./0.05 Torr).

Since in the alkylation of 1-substituted-3-hydroxy-1H-indazole sodium salts a small amount of the isomeric 1-substituted-2-alkyl-indazolones (II) is formed (J. Med. Chem. 9, 38, 1966) in this distillation both the low boiling impurities, as a head, and the above mentioned impurities, as a tail, are removed.

This so purified base is then transformed into the corresponding hydrochloride, using conventional methods, and it is recrystallized from suitable solvents.

In industrial practice the distillation of the base was found to be not convenient both economically because of the unusual reduced pressure which would be required in order to avoid decomposition and because it is impossible, in the time required for industrial distillation, to avoid a slight, but noticeable decomposition which causes a loss of product even if working at 0.05 Torr.

We found that the mentioned raw viscous residue can be used without distillation to obtain (I) as hydrochloride. This operation can be accomplished by dissolving the residue in n. hexane or similar aliphatic or cycloaliphatic solvents, as pentane, heptane, cyclohexane or mixtures of $C_5$–$C_{10}$ paraffins or cycloparaffins, in which the isomeric impurity is insoluble, and adding gaseous HCl to the solution, then by collecting the crude hydrochloride and recrystallizing it from ethanol or from any other low alcohols.

But the hydrochloride thus obtained shows the presence of 300–500 ppm of 1-chloro-3-dimethylaminopropane hydrochloride as shown by the Gas-chromatographic analysis.

The presence of this impurity, which is an alkylating agent, made the product not suitable for medical use. It is indeed well known that alkylating substances are generally suspected to be carcinogens. We tried several unsuccessful ways to avoid this inconvenience. First of all we studied the effects of a single recrystallization from several anhydrous or aqueous solvents on a sample of Benzydamine hydrochloride contaminated by 500 ppm of said impurity.

The following Table shows the results obtained.

| SOLVENT | CONTAMINANT (ppm) | |
|---|---|---|
| | In starting product | In final product |
| ISOBUTANOL containing 2% $H_2O$ | 500 | 186 |
| ISOBUTANOL containing 5% $H_2O$ | 500 | 85 |
| n-BUTANOL | 500 | 280 |
| 95% ETHANOL | 500 | 158 |

Then we studied the effects produced by repeated recrystallizations. After five recrystallizations from ethanol we obtained (I) hydrochloride still contaminated by 50 ppm of the same impurity.

This amount resulted to be still too high to be accepted. Moreover this procedure took a too long time and considerably reduced the final yield. Several water washings of the crude raw residue of (I) base also resulted to be unsuccessful since 1-chloro-3-dimethylaminopropane showed a high partition coefficient between the xylenic solution of (I) and water.

In fact also after twenty washings of the crude base with a volume of water equal to 1/10 of the weight of the base, each time, the hydrochloride obtained resulted to contain an unacceptable amount (about 150 ppm) of the impurity.

In another effort we added to the xylenic solution of the crude benzydamine base a certain amount (about 0.5%) of dimethylamine and we refluxed this mixture for about one hour in order to destroy the excess of 1-chloro-3-dimethylaminopropane.

After this operation, the washings of the xylenic mixture and the normal working up (avoiding distillation), we obtained a benzydamine hydrochloride which was still contaminated by 20–30 ppm of the alkylating agent.

Finally we found that, although 1-chloro-3-dimethylaminopropane is well soluble in water and its boiling point is higher than that of the water (134°–5° C./765 Torr) (Bl. 4, 148), it can be easily and completely removed simply by treating the raw base with steam before or after n.hexane extraction.

To be more clear, the steam is bubbled into the crude residue; a certain amount of steam is condensed in the reactor and this amount is related more to the geometry and thermal characteristics of the reactor rather than to the quantity of crude base to be purified. Another amount is distilled and condensed in the refrigerator. In order to obtain a base from which it is possible to obtain a hydrochloride containing an amount of the impurity below the sensitivity-limit of the analytical method employed (10 ppm), it is sufficient to collect in the distillate a quantity of water equal to 1/5 of the weight of the raw base to be purified.

In industrial practice this quantity will be optimized depending on the quantity of the crude base to be treated and on the characteristics of the reactor; but, if such quantity of water will be too small the purification will be inadequate; on the contrary if it will be too much there will be an useless waste of energy to produce steam. This purification method showed to be, in industrial practice, rather advantageous because it is not time expending, and showed a minimum loss of the desired product only in the final recrystallization.

EXAMPLE I

The sodium salt of 1-benzyl-3-hydroxy-1H-indazole (15 g) was suspended in xylene (130 ml). A solution of 1-chloro-3-dimethylaminopropane (6.5 g) in 10 ml of xylene was rapidly added. Additional 2 g of the same chlorobase from the same xylenic solution were added after a 2 hours heating. A third 2 g portion was added after one hour's interval and the mixture was refluxed for 4 more hours.

After this time the mixture was cooled, washed thrice with 50 ml of water each time, and the xylene was distilled off.

Steam was bubbled into the crude residue (20 g) until 4 ml of water were distilled off. After cooling n.hexane (100 ml) was added to the remaining mixture. The aqueous phase was discharged and the hexane solution, after treatment with charcoal, was filtered.

Gaseous HCl was then bubbled into the hexane solution until pH3 was reached. The precipitated hydrochloride was collected by suction and recrystallized by isobutanol containing 5% $H_2O$. 15.5 g (yield 73.6%) of benzydamine hydrochloride (m.p. 159.5° C. on Mettler F P5) were obtained. A GC analysis showed no presence of 1-chloro-3-dimethylaminopropane (sensitivity of the method=10 ppm).

EXAMPLE II n.Hexane (100 ml) was added to the crude residue as obtained in Example I, the organic phase was separated, the solvent was removed and the residue was treated with steam until 4–5 ml of water were collected.

After steam-distilling the water was decanted from the residue which was dissolved in isobutanol (50 ml) and a quantity of concentrated hydrochloric acid, suitable to obtain pH3, was added to the solution. The precipitated hydrochloride was collected by suction and washed with isobutanol: 15.2 g (yield 72.1%) of benzydamine hydrochloride were obtained (m.p. 159.3° C. on Mettler F P5). A GC analysis showed no presence of 1-chloro-3-dimethylaminopropane (sensitivity of the method=10 ppm).

What we claim is:

1. An improvement in the process of removing final residues of 1-chloro-3-dimethylaminopropane from a mixture of said propane with 1-benzyl-3-dimethylaminopropoxy-1-H-indazole (benzydamine) which comprises treating said mixture with substantially about 20% by weight of steam, and removing said 1-chloro-3-dimethylaminopropane from said miture with the steam.

2. A method for preparing substantially pure benzydamine hydrochloride from purified benzydamine synthesized by condensing 1-chloro-3-dimethylaminopropane with 1-benzyl-3-hydroxy-1H-indazole sodium salt and collecting a crude condensate which comprises (A) steam distilling the crude condensate product until an amount of distillate equal to about twenty percent by weight of said crude product is collected then (B) dissolving the resulting product in an amount of n-hexane sufficient to substantially dissolve all benzydamine and leave behind isomeric impurities and then (C) treating the substantially water free n-hexane solution with hydrochloric acid to obtain the product.

3. A method as in claim 2, wherein step (B) is performed before step (A).

4. A method as in claim 2, wherein said resulting benzydamine comprises:
   less than 10 ppm of 1-chloro-3-dimethyl-amino propane.

5. A method as in claim 3, comprising;
   adding about 100 mls of n-hexane to the crude condensate, separating the organic phase and treating the residue with steam until 4.5 mls. of water are collected, acidifying the mixture with hydrochloric acid and
   collecting precipitated hydrochloride of benzydamine.

6. A method as in claim 2 where the reaction medium is acidified to pH 3 in the acidification step.

* * * * *